United States Patent
Killin et al.

(10) Patent No.: US 7,169,085 B1
(45) Date of Patent: Jan. 30, 2007

(54) USER CENTERED METHOD OF ASSESSING PHYSICAL CAPABILITY AND CAPACITY FOR CREATING AND PROVIDING UNIQUE CARE PROTOCOLS WITH ONGOING ASSESSMENT

(75) Inventors: James P. Killin, San Jose, CA (US); Paul Christensen, San Jose, CA (US)

(73) Assignee: Therapy Pro Inc., San Jose, CA (US)

( * ) Notice: Subject to any disclaimer, the term of this patent is extended or adjusted under 35 U.S.C. 154(b) by 0 days.

(21) Appl. No.: 11/233,755

(22) Filed: Sep. 23, 2005

(51) Int. Cl.
*A63B 21/00* (2006.01)
*A63B 22/00* (2006.01)

(52) U.S. Cl. .......................... 482/8; 482/148; 482/900; 434/247; 600/595

(58) Field of Classification Search ............... 482/1–9, 482/900–902; 600/300, 481, 484, 587, 595; 434/247
See application file for complete search history.

(56) References Cited

U.S. PATENT DOCUMENTS

| | | |
|---|---|---|
| 5,553,609 A | 9/1996 | Chen et al. |
| 5,810,747 A | 9/1998 | Brudny et al. |
| 6,007,459 A | 12/1999 | Burgess |
| 6,206,702 B1 | 3/2001 | Hayden et al. |
| 6,436,058 B1 | 8/2002 | Krahner et al. |
| 6,607,497 B2* | 8/2003 | McLeod et al. ............ 600/595 |
| 6,609,523 B1 | 8/2003 | Anthony |
| 6,613,000 B1 | 9/2003 | Reinkensmeyer et al. |
| 6,626,800 B1* | 9/2003 | Casler ........................ 482/8 |
| 7,074,168 B1* | 7/2006 | Farnes et al. ............... 482/148 |
| 2001/0050088 A1 | 12/2001 | Leeds et al. |
| 2002/0082143 A1 | 6/2002 | Leeds |

OTHER PUBLICATIONS

U.S. Appl. No. 09/360,225, Scheirman, Aband-Unpublished.

* cited by examiner

*Primary Examiner*—Glenn E. Richman
(74) *Attorney, Agent, or Firm*—Pillsbury Winthrop Shaw Pittman LLP (57) ABSTRACT

A system and method are disclosed for assessments, which can be self-conducted or performed with the assistance of a healthcare provider. The system and method assist a user to interact with a user-centered system utilizing the musculoskeletal system as a basis for generation a protocol for treatment for wellness, general health, diseases, pre employment physical capacity tests, prevention of repetitive stress, absence management, worker's compensation cost control, disease management, conditions, and athletics. The system and method disclosed assist the user in performing both physical or function capability assessment as well as physical or functional capacity assessment.

18 Claims, 8 Drawing Sheets

USER CENTERED METHOD OF ASSESSING PHYSICAL CAPABILITY AND CAPACITY FOR CREATING AND PROVIDING UNIQUE CARE PROTOCOLS WITH ONGOING ASSESSMENT

BACKGROUND

The present invention is related to health care and more specifically to a user centered method of assessing functional and physical capacity and evaluating the ability of a person to perform activities of daily living based on health concerns, diseases, disabilities, injuries, surgeries and presenting a continuum of care protocol with ongoing assessments and outcome analysis.

During the past few decades the demand for physical therapy services has risen. These services have typically been limited to exercise therapy under the direct supervision of a medical professional. Injury victims, including those experiencing pain or limited functional capacity or even immobility, commonly see a physical therapist during medical treatment and expect the therapist to address the pain and/or their functional capability that has resulted in reduced mobility. During a typical physical therapy session, the therapist assesses a client's physical situation by reviewing the relevant medical records and by direct assessment of the client. Based on the combination of information gathered from medical background and direct assessment the therapist will provide an exercise protocol along with a plan of care. However, a limitation of providing physical therapy generally is that the therapist and the client need to be located together. This restricts the access of some users to therapists. An alternative solution would be to provide a traveling therapist. However, this places significant time limitations on how many clients a traveling therapist can visit in a day due to time spent traveling.

Yet another alternative is telemedicine. Telemedicine is an idea that has drawn recent attention from military, government, medical professionals, insurers and computer/software specialists. Telemedicine is the provision of health care consultation and education using telecommunication networks to communicate information, and practice medicine via telecommunications and interactive video technology. Telemedicine typically involves the real time or near real-time transfer of medical information between places.

In addition to telephone based services, the Internet has given birth to a variety of sites that provide information to anyone desiring to improve their physical fitness. One such site, iFIT.com, provides for interactive one-on-one personal training. The instructor can walk the user through the training session via a pair of computers, each with video capability. However, this has the limitation of requiring a person to interact with the user and the limitation of the user having the necessary video capability.

Personal on-line training programs or competing in virtual races are also available to users. However, these programs do not take into account the physical condition of the user and do not provide a means for assessing the user's ability prior to providing the exercise program. These on-line training programs allow the user to train at home minus the equipment you would find in the fitness club. However, these program typically do not take into account tailoring a program based on the user's physical condition. Other on-line services provide videos for specific injuries and conditions, but again fail to specifically assess the user's physical condition. For example, various services exist that provide a video library that can be used by users and clinicians to customize exercise programs. For example, patent applications filed include Leeds et al., U.S. Publication No. 2002/0082143, published Jun. 27, 2002, U.S. application Ser. No. 09/360,225, and Leeds et al., U.S. Publication No. 2001/0050088, published Dec. 13, 2001.

Other known systems and methods link a care giver to a user using visual and audio communication. For example, Chen et al., U.S. Pat. No. 5,553,609 discloses a network employing audio-visual technology to link a user with a remote care-giver. Data and video are transferred between the caregiver and the user to enable the user to have access to a remote, or multiple remote caregivers. The network includes a database with accessible user information to assist caregivers in diagnosis and treatment. The network relies on bodily condition sensors and other appliances, which may be controllable by the caregiver, to monitor a user. However, such systems are faced with limitations that prevent cost effective delivery of services to users. For example, the video technology, in particular, is remotely controlled to enable the caregiver to visually search particular areas. Another reason for the high cost is that the care giver needs to monitor the user using, for example, the audio technology that enables the caregiver to listen to sounds made by the user.

Known methods of providing physical therapy services are costly and not readily available. Additionally, current systems and methods do not provide a tool that is responsive to surgical needs and related capability of the user as well as the user's capacity. Also individual efforts to comply with an independent assessment program are poor because of inadequate follow-up materials to be reviewed by the user and because of the lack of progression information given to the patient.

Therefore, what is needed is a system and method for user generated exercise prescription that allows a user to self assess based on a specific injury, condition, disease, goal or surgery and generate an exercise protocol, allowing the user to view it and if desired, customize the protocol in accordance with the user's requirements and exercise tools available. Furthermore, there is a need to provide such services cost effectively and make them readily available while taking into consideration the physical condition of the user. There is also a need to enable a user to have their records transferred to various health care providers so that the user may see any of a number of physical therapists without undue burden.

SUMMARY

A system and method are disclosed for generating an exercise prescription based on a user's self assessment related to functional capacity, physical performance goals, specific injury, health condition, disease, goal or surgery. The present invention generates an exercise protocol, based on that assessment performed by the user allowing the user to view the protocol and if desired, customize the protocol in accordance with the user's requirements and the exercise tools available to the user. The assessments and applicable related exercise and care plans are provided directly to the users, with or without caregiver intervention. The information provided is based on capability, physical performance goals, functional capacity, specific injury, surgery, disease or health condition while providing feedback to the user and healthcare provider.

Self-management is considered the cornerstone of the overall management of many chronic conditions since access to medical care, including education, is often limited because of time, distance and financial constraints. This system empowers the user to appropriately care for themselves. Compliance is a major reason for failed self care. A primary cause of non-compliance is lack of accurate reinforcement to ensure home exercise is performed properly.

Assessments and related exercise and plans of care are both fact and time based and provide exercise regimes that can be modified by the user within acceptable ranges, which is monitored by the system according to the teaching of the present invention. The exercise protocols are generated by algorithm-based assessments completed by the user. Data, including medical and personal history, disease, injury, surgery, medical condition or physical requirements are entered by the user along with responses to functional capacity questions based on specific single or multiple areas of anatomy. Assessment questions are movement or exercise based and used to evaluate functional capability and capacity; each question can be a used to provide an assessment. For example, one question, such as the ability to pick something up, may be sufficient to provide an exercise specific for that activity, while a series of questions form an important part of a total assessment test. Based on a patient's complete assessment, algorithms that use the answers automatically determine the exercise and care plan specific to that individual. The care plans, which may include exercises, body mechanics and treatments, are presented using audio and video delivered by Web, DVD, TV, radio frequency, satellite and other medium to give the user the ability to perform directed exercise therapy anytime, anywhere.

The disclosed method extends and expands the reach of clinicians by standardizing care for common rehabilitation treatments and education by automating clinically driven prevention and treatment by utilizing health risk assessments, evaluations, scales, practice guidelines and user empowerment strategies with users receiving personalized education and care plans based on profiles and physical risk assessments.

The system utilizes a communication link between the system and the user, which includes sound and video treatment reinforcement as well as assessment and outcome management reporting to authorized healthcare providers and third party payers. Accordingly, assessments are performed on an ongoing basis directed by the system and exercise protocols adjusted accordingly and the user status communicates to healthcare providers, payers and employers electronically. The system according to the present invention directs the user for timing of a schedule assessment and automatically notifies the user. However, an alternative embodiment of the present invention allows the user or any other authorized user to perform the assessment as often as desired or necessary to provide the proper protocol, especially as the capability or capacity of the user changes.

The present invention also provides computer guided questions, the answers to which provide time based assessments resulting in exercise therapy and related care plans for specific wellness, general health, diseases, pre-employment physical capacity tests, prevention of repetitive stress, absence management, worker's compensation cost control, disease management, conditions and athletic activities to increase activities of daily living, correct impairments and evaluate and improve physical and functional capabilities and/or capacities.

BRIEF DESCRIPTION OF THE DRAWINGS

These and other aspects and features of the present invention will become apparent to those of ordinary skill in the art upon review of the following description of specific embodiments of the invention in conjunction with the accompanying figures, wherein.

DETAILED DESCRIPTION

The present invention will now be described in detail with reference to the drawings, which are provided as illustrative examples of the invention so as to enable those skilled in the art to practice the invention. Notably, the figures and examples below are not meant to limit the scope of the present invention to a single embodiment, but other embodiments are possible by way of interchange of some or all of the described or illustrated elements. Moreover, where certain elements of the present invention can be partially or fully implemented using known components, only those portions of such known components that are necessary for an understanding of the present invention will be described, and detailed descriptions of other portions of such known components will be omitted so as not to obscure the invention.

In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

The present invention includes a system of user directed assessments and evaluation scales along with clinically accepted post surgical protocols supported by a database library of treatments based on specific phases of rehabilitation and the related goals, including rehabilitation exercise videos, precautions, utilization of assistive devices, and other therapeutic treatments. The system performs the assessment to determine a user's physical capability as well as functional capacity, wherein capability is a determination of the user's ability to perform a particular task using a specific part of the body and capacity measures how well or with what degree of difficultly the person performs the assigned task with the part of the body. The user communicates with the system through a communication device. The scope of the present invention is not limited by the type of device used to communicate with the system. For example, the user can communicate with the system using an interactive or web-enabled television (TV), an interactive Digital Video Disk (DVD), fill out and fax a form, use a touchtone phone to manually enter responses.

Figure 1:
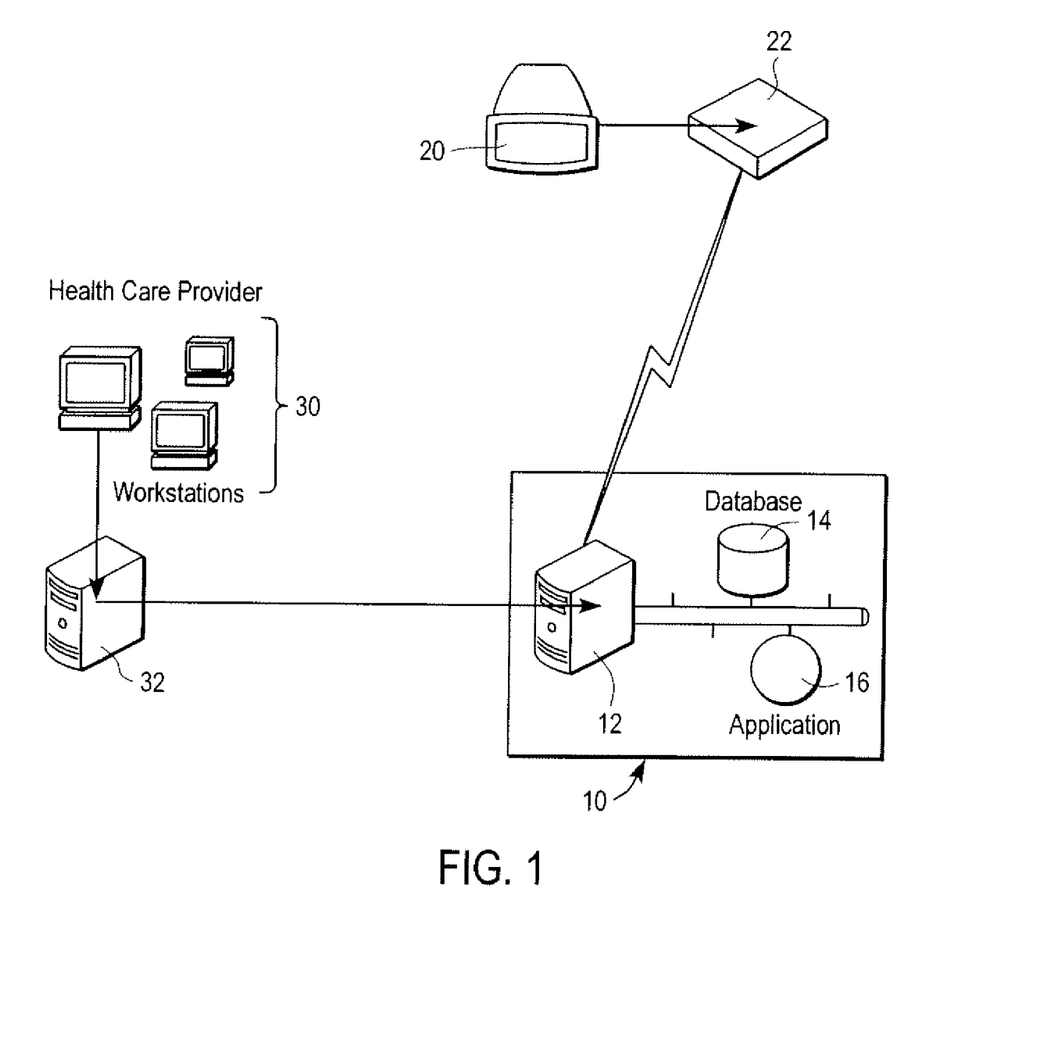
FIG. 1 shows a system that includes an interactive television for use by a users in accordance with the teachings of the present invention.

Referring now to FIG. 1, a system 10 includes an access point 12, a database 14 and an application program 16. In one embodiment, the access point 12 is a server, which can be one computer or multiple computers working together, that is in communication with the database 14 and the program 16, each of which can be hosted on the same or different computers or at different locations. The term "remote location" is used to refer to locations that are different from the access point 12, though they may be in the same facility as the access point (such as exercise stations in a hospital that are configured on the hospital communication network) or even more geographically remote (such as devices that are configured to communicate using the Internet or other networks). In an alternative embodiment, the access point 12 hosts the database 14 and the program 16. The access point 12 is also in communication with television 20 through a DVD/computer 22 that also can function with router capability. Additionally, the access point 12 is in communication with third parties or health care providers 30 through a server 32. Each user can access the program 16 through the workstation 20 and perform the assessment program, the results of which are stored in the database 14 and can be accessed by the user or an authorized health care provider. In this way the user's information and history can be stored at one location and accessed from a different location.

Figure 2:
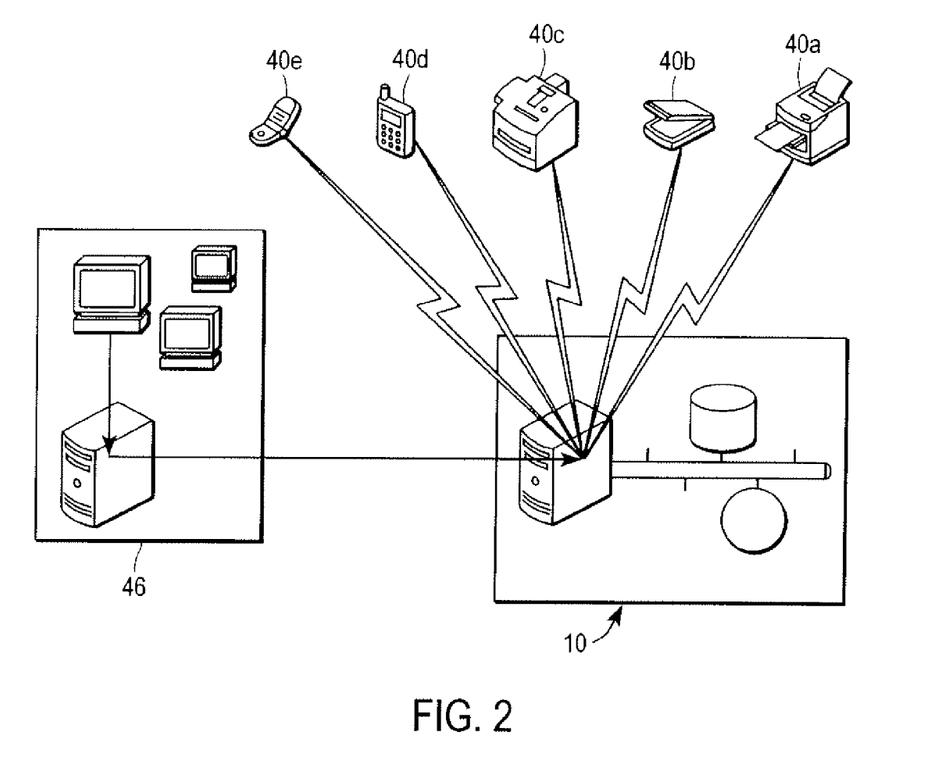
FIG. 2 shows a system that includes communication devices for use by a users in accordance with the teachings of the present invention.

Referring now to FIG. 2, the system 10 of FIG. 1 is shown in communication with devices 40a–e, each of which can be used to bi-directionally communicate with the system 10, including the communication of user information. The devices 40 include a printer, a scanner, a multi purpose printer and facsimile machine, a digital wireless communication device, and a cellular or wireless telephone. However, as indicated above, the scope of the present invention is not limited by the type of device communicating with the system 10 or the type of communication. For example, one of the devices 40 may communicate with the system 10 via a wireless communication while another communicates with the system 10 using a landline.

The user can perform an assessment, preferably in substantially real-time at a single session, and using any of the devices 40 to communicate the information to the system 10, wherein the application program will receive and read the data that is later stored in the database. The user can also communicate answers or responses through a Personal Digital Assistant (PDA) or a wireless phone. In yet another embodiment the user would respond, as prompted, to the questions that are verbally presented. In an alternative embodiment, the user can respond to prompts from the system 10 based on a list of written questions that the user previously received. Accordingly, the user can receive the questions in advance and conduct the assessment using a telephone having Dual Tone Multi-Frequency (DTMF) functionality. Additionally, the system 10 is in communication with third parties or health care providers 46. Accordingly, the user's medical history and the results of the user's assessment can be directly communicated to the health care provider 46 thereby allowing a user to complete an assessment and instantly provide the results of the assessment to the health care provider 46.

Figure 3:
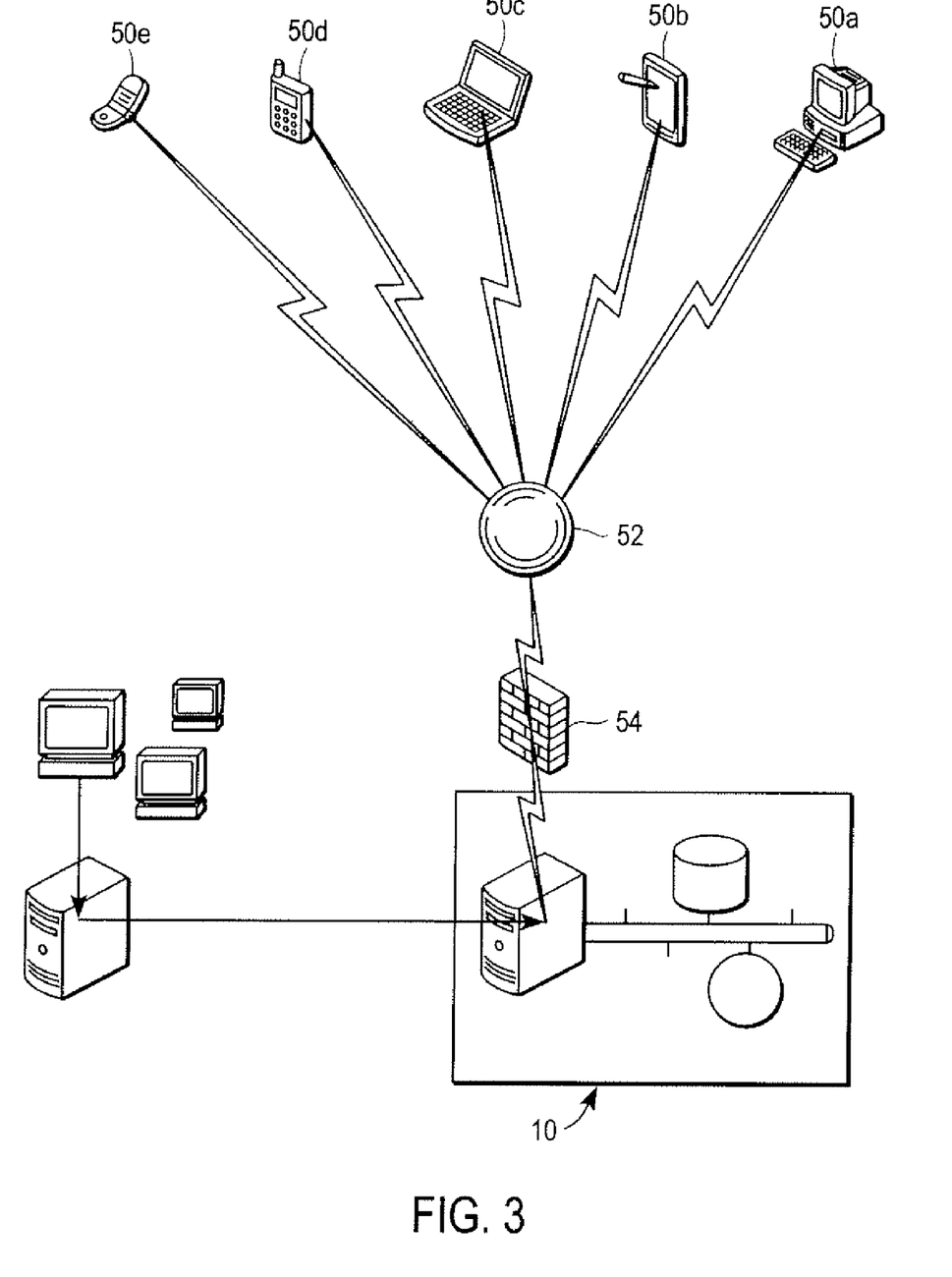
FIG. 3 shows a system that includes communication through the Internet by a remote users in accordance with the teachings of the present invention.

Referring now to FIG. 3, the system 10 of FIG. 1 is capable of communicating with a plurality of devices 50a–e. The devices 50a–e are each capable of communicating with the system 10 through the Internet 52 or some other network and the firewall 54. Additionally, for security reasons, each of the devices 50 are authenticated by the system 10 an allowed to communicate with the application program of the system 10 as well as retrieve information from the database of the system 10.

Figure 4:
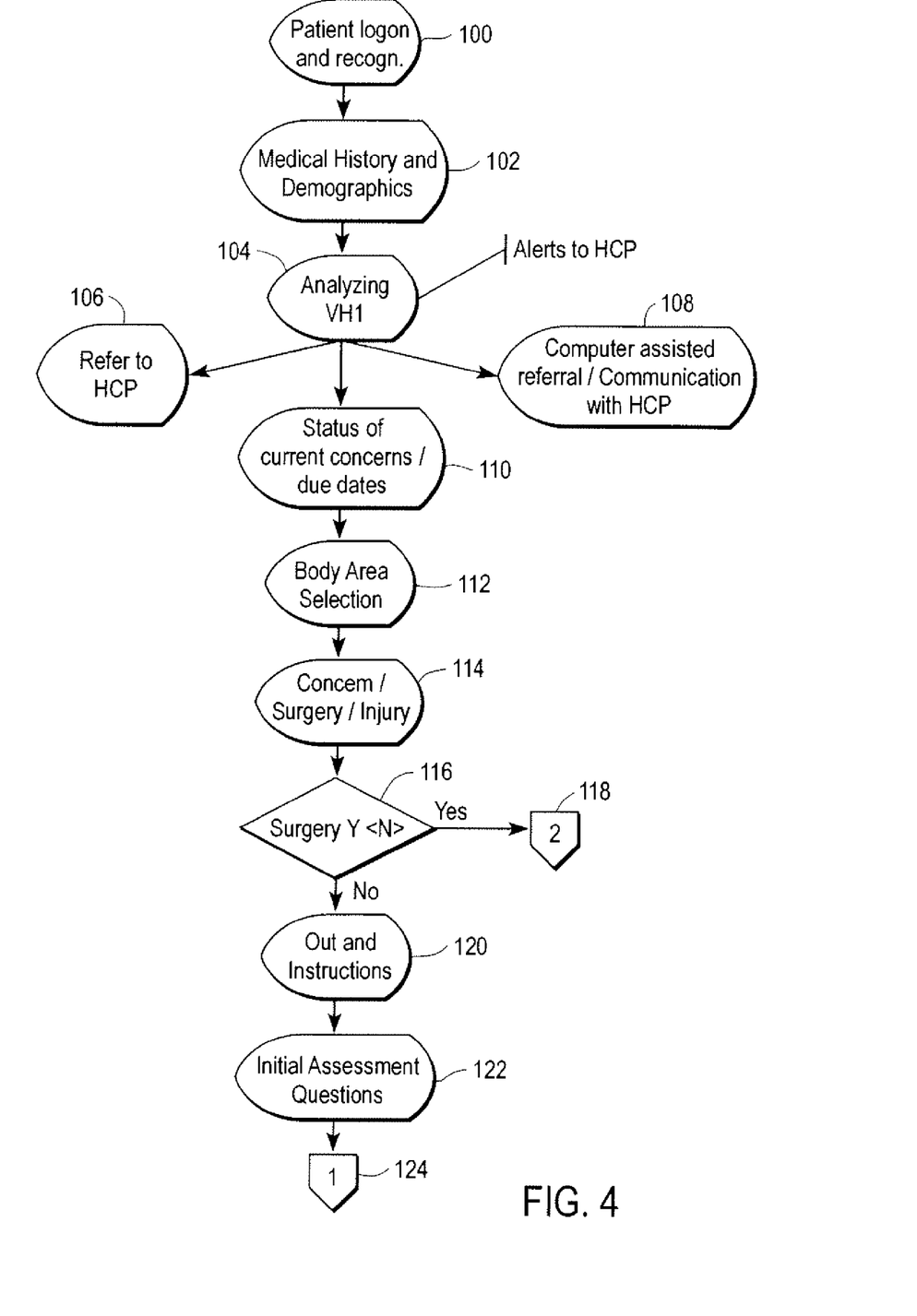
FIG. 4 is a flowchart showing the initial data gathering through initial assessment in accordance with the teachings of the present invention.

Referring now to FIG. 4 the process of gathering data from the user begins at step 100 wherein the user logs onto the system. The user may be communicating with the system via DVD, Web, television satellite radio frequency and utilizing a variety of receiving mechanisms including a computer, television, cell phone, PDA or other such hardware that allows communication of audio and video information. The system and algorithms, which are part of the system and are described, further herein, allow elimination of the need for face-to-face interface with a health care provider or physical therapist. Once the user has successfully logged onto the system, then the user has access to their past information, status information, and the ability to utilize the exercise protocols and assessments tools. The system may guide the user through a series of question in order to assess the capacity and capability of the user, especially given that the system can provide a protocol to meet the needs of a user with limited physical capacity as well as a user preparing for athletic competition or guide them to a specific post surgical protocol. At step 102, the user will enter their medical history and demographics. If the user is a new user, then the user will enter all of the related information. On the other hand, if the user has already entered information or is a returning user, then the user will update existing information as necessary. At step 104, the system analyzes the information provided by the user or the User History Information (UHI).

One example of the information provided and the analysis performed is related to the ankle specific medical history as shown below. The user responds to a series of questions as follows:

---

If this is the same injury you have used TherapyPro for in the last 6 months, then go to the functional ankle scale
General health perception
(0 = total disability and 10 = is without any physical limitation)
0   1   2   3   4   5   6   7   8   9   10
Current level of physical fitness
(0 = cannot move, 10 = competitive athlete)
0   1   2   3   4   5   6   7   8   9   10
Circle an activity level that best describes your typical level of activity.
Sports:    sedentary    recreational    competitive
Work:      sedentary    light           moderately    heavy (construction) heavy
What is your current functional level compared to your level prior to this injury?
10%   20%   30%   40%   50%   60%   70%   80%   90%   100%
Does another injury limit your functional capacity prior to the current injury   Y   N
If yes, what level of unrestricted function were you prior to this injury
10%   20%   30%   40%   50%   60%   70%   80%   90%   100%
Please assess this other injury as well to have a complete exercise program
to improve your condition.
Please indicate where this injury is and assess it also in order to have a complete program design.

-continued

1. Did the pain begin for no apparent reason? Y   N
2. Do you have pain while inactive? Y   N
3. Do your currently have a fever, infection, swelling in the ankle or general body aching? Y   N
If yes to any of the above 3 questions, you should have additional medical screening for other potential problems.
If you have had additional screening and have been cleared to participate in a rehab program, please continue.
Do you have numbness, tingling or pain in your thigh, leg or foot that change with changes in posture, position or activity? Y   N   If Y, then also use low back exam to clear possible referral of symptoms.

Information may be received from the user by phone, fax, web, email, personal digital assistant, or any other electronic method and associated device for transmitting data and automatically interfaced with the system. Information is stored in the system's database and sorted based on any number of criteria, including user name, date, concern, surgery and injury. The algorithms determine whether the user should proceed with the system or stop using the system and be referred to a health care provider. By algorithms, as used herein, is broadly meant a manner of attributing the proper weight to the various inputs that are used in the determination of the appropriate exercise, as well as other factors, such as the amount of time since the injury and/or surgery. Different algorithms are determined for usage with a specific area of the body and based on the weighting of answers to specific questions that either individually, as a group or in total, will determine the exercises or phase of care and related exercises and care plans appropriate based on the answers of the user. For ease of usage, the term "algorithms" is used herein, but it should be understood that not all assessments will use all algorithms, but typically different algorithms are created for the assessments dealing with a specific area of the body. Thus, the number of questions and weighting of those questions relative to each other and any other criteria is preferably made for each different specific body area. In one embodiment, a score of either an individual question, group, or total number of questions is then applied to a specific scale, based on the specific area to determine the appropriate exercises and plan of care. For instance A1+B2+C3+D4=total score, where A, B, C and D are weights to the values associated with questions 1, 2, 3, and 4. This will give a scaled score, which score can then be measured for the range of scores possible, and, based upon that, the appropriate exercise routine selected automatically. Questions can be weighted based upon many factors, such as relevance to the particular assessment and/or time since the injury and/or surgery. As the user performs a reassessment, a recalculation is preferably performed to determine an updated exercise or plan of care.

If the algorithms determine that the person should be referred to a health care provider, then at step 106 the user is provided instructions to contact a health care provider. In one embodiment, the user would simply receive instructions to contact a health care provider, while in another embodiment, the user is provided with a choice of health care providers located near the user and at step 108 the information provided by the user, in response to the questions, is forwarded to the healthcare provider selected by the user.

Figure 6:
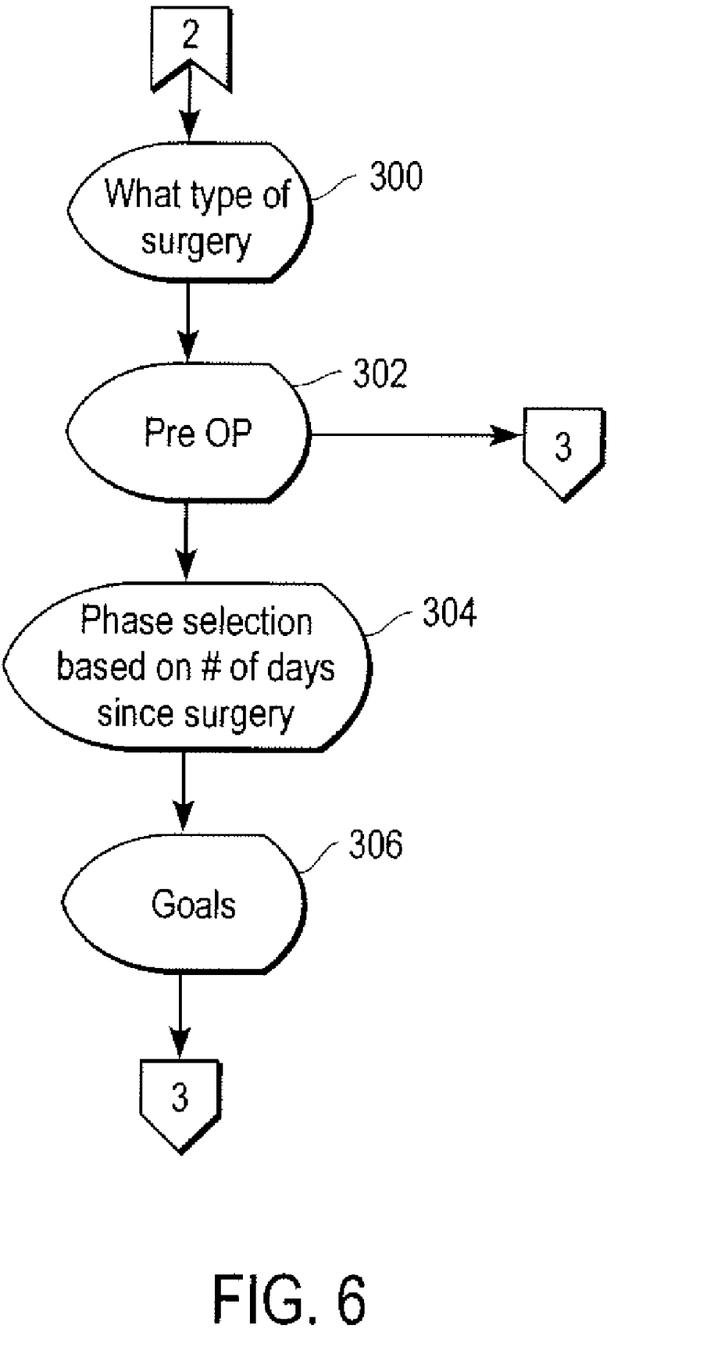
FIG. 6 is a flowchart showing the process of evaluation and determination of exercise protocols for post surgical exercise in accordance with the teachings of the present invention.

If the user was referred to a healthcare provider during a previous assessment, then the system checks to make sure that the user has a physician clearance. Alternatively, if the user was referred to a healthcare provider and the user elects to continue, then the system checks to determine if a user already obtained a physician clearance prior to beginning the assessment program. If the user is a returning user, then at step 110 the current status of all exercise assessments for individual specific areas are noted with specific requirements and actions for the user to perform. At steps 112 and 114, the user selects the specific area(s) of the body and date of the injury, trauma or surgery along with the specific concern, injury or surgery. For example, in one instance the goal of the user may be to jump higher. Thus, the protocols established based on the assessment performed will be to enhance or improve the user's vertical leap. In another instance the user may be recovering from an injury, which will result in a protocol specific to the needs of the user based on the assessment. At step 116, the system queries the user to determine if the user has had surgery. If so, then at step 118 the system will move the user to a separate assessment program routine that handles the process of evaluation and determination of exercise protocols for post surgical care, as shown in FIG. 6. If it is determined that the user is not having or has not recently had surgery, then at step 120 the non-surgical users are given instructions via audio, text and video on program use and questions, which if answered appropriately will allow the user access to the program routine for non-surgical users. If the answer is not appropriate for continued use, the user is referred to a health care provider. The system provides a set of instruction in order to initiate the assessment and help the user to perform a self assessment and answer a series of questions.

At step 122, the initial assessment, which is based on the specific body area selected by the user, uses algorithms to evaluate the user's ability to proceed with additional testing and the program. Assessment information is stored and tracked for analysis and for reporting to a third party as described the process set forth in FIG. 5. In order to assist the user in performing the assessment test and report the results, the assessment process uses video, text and audio to assist the user in performing the tests.

Figure 5:
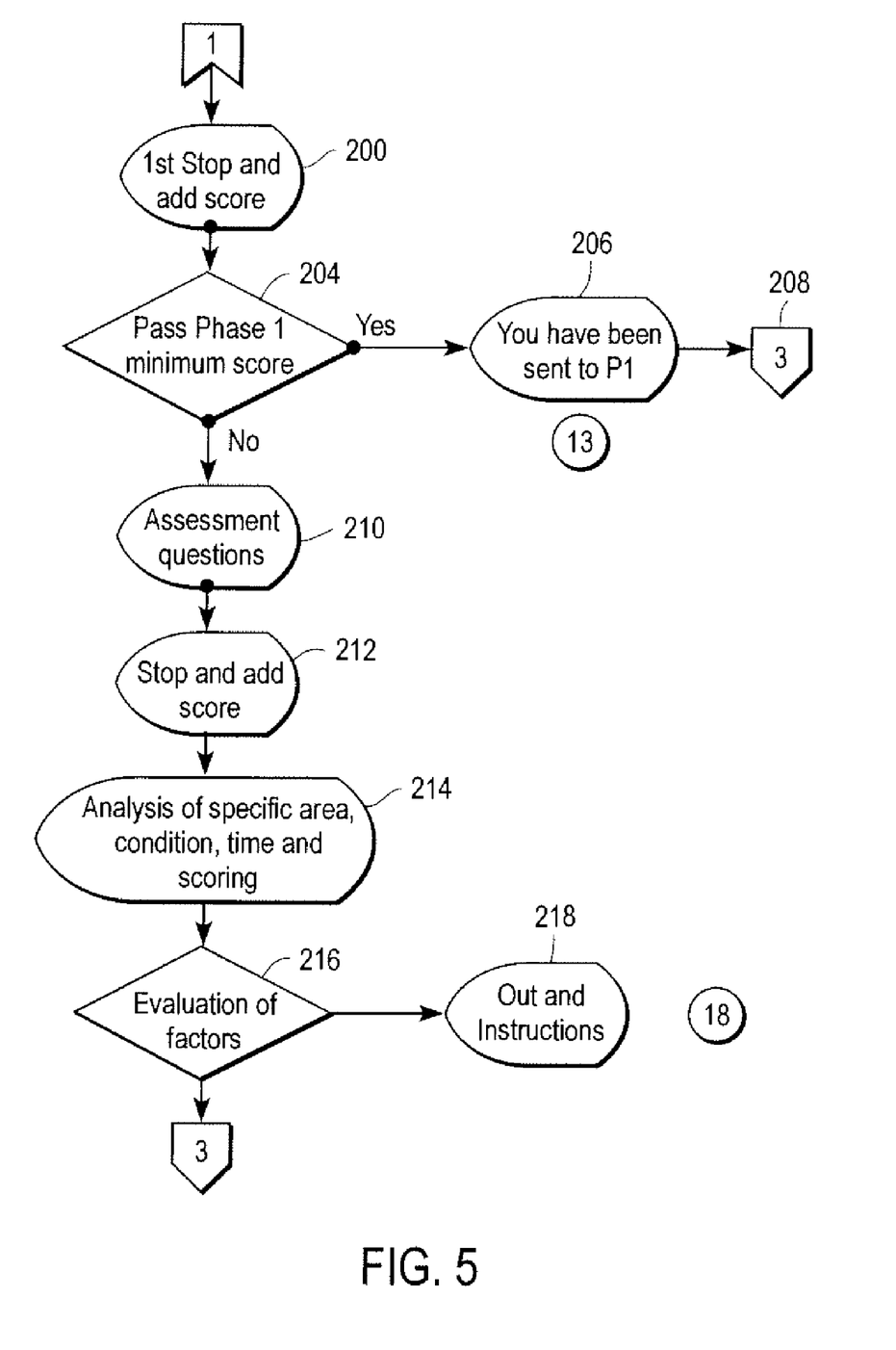
FIG. 5 is a flowchart showing the second assessment and scoring in accordance with the teachings of the present invention.

Referring now to FIG. 5, at step 200 a categorical scoring based algorithm specific to each musculo-skeletal area is used to evaluate and determine if a user should be classified as a Phase 1 user, with Phase 1 being the lowest on a scale of Phase 1 to Phase 5. The assessment includes at least two components that are used to determine the phase at which a user is placed. In one part the questions as a whole are grouped and scored while in another part of the assessment each question is individually weighted such that certain response to each of the assessment questions may result in the user being placed in a particular phase or moving on to answer additional assessment questions. At step 204, if the user is classified as a Phase 1 user, then the system will utilize a process specifically targeted at a Phase 1 user.

Continuing with the example provided above, an example of the initial assessment for the ankle with the associated point scale is as follows:

Pain: Please rate your pain

40 - No Pain
30 - Occasional pain, no compromise of activities
20 - Mild pain, limits recreational/work activities, activities of daily living are Unlimited
10 - Painful, activities of daily living are difficult
 0 - Painful, cannot do any activity -continued Range of Motion: Perform tests with your knee straight and compare to the
uninjured ankle 40 - No limitations of motion
30 - Can fully point foot away from and towards your knee and can turn foot inward and outward with mild pain
20 - Can fully point foot away from and towards your knee and can turn foot inward and outward with moderate pain
10 - Can fully point foot away and toward your knee but cannot turn foot inward or outward
 0 - Cannot fully point foot away from or toward your knee
Weight bearing: Please rate your ability to bear weight on your injured side 40 - No limitations
30 - Can walk on injured side, but running is impaired
20 - Can stand on injured side alone, but walking is impaired
10 - Cannot stand on injured side alone, and walking is impaired
 0 - All activities are performed without weight bearing on the injured side
Assistive devices: Please rate your need for assistive devices 50 - No need for assistance
40 - Use a brace for physical activities
30 - Use a brace only for community walking
20 - Use a brace & cane/crutch for walking in the home
10 - Use a cane/crutch for all activity
 0 - Wear a brace and use a cane/crutch at all times
Swelling: Mark the lowest activity level which causes swelling 40 - Only after sporting activities
30 - After standing or walking >30 minutes
20 - After standing or walking <30 minutes
10 - After sitting, ie at a desk
 0 - At all times The related scoring in the example of the initial assessment in FIG. 4 would be displayed in audio and video along with text. The system automatically takes the user to the appropriate Phase of care for the specific concern and body area. An example of an initial assessment as reported to the user is shown in the text below:

Stop Here: Your score is 30 or less, *STOP*. Go to Exercise Program Phase 1. DO NOT continue with the rest of this assessment.

Continuing with FIG. 5, at step 210, the second level of assessment is based on specific body area and the assessment uses algorithms to evaluate the user's ability to proceed with additional testing. The system uses video, text and audio to assist the user in performing the assessment tests. At step 212, the system uses a categorical scoring based algorithm specific to each musculo-skeletal area to evaluate and determine where a user should be classified on a scale of Phase 1 to Phase 5. The scoring methodology includes information from the first and second assessments. The system includes weighted scales that are unique to each of the assessment steps. Each of the user's responses result in a unique question/answer combination that is reflective of the level of movement and hence the level of capacity and/or capability. This combination has an assigned number or weight that results in a scoring mechanism, which is used to determine the phase assigned to the user.

Figure 7:
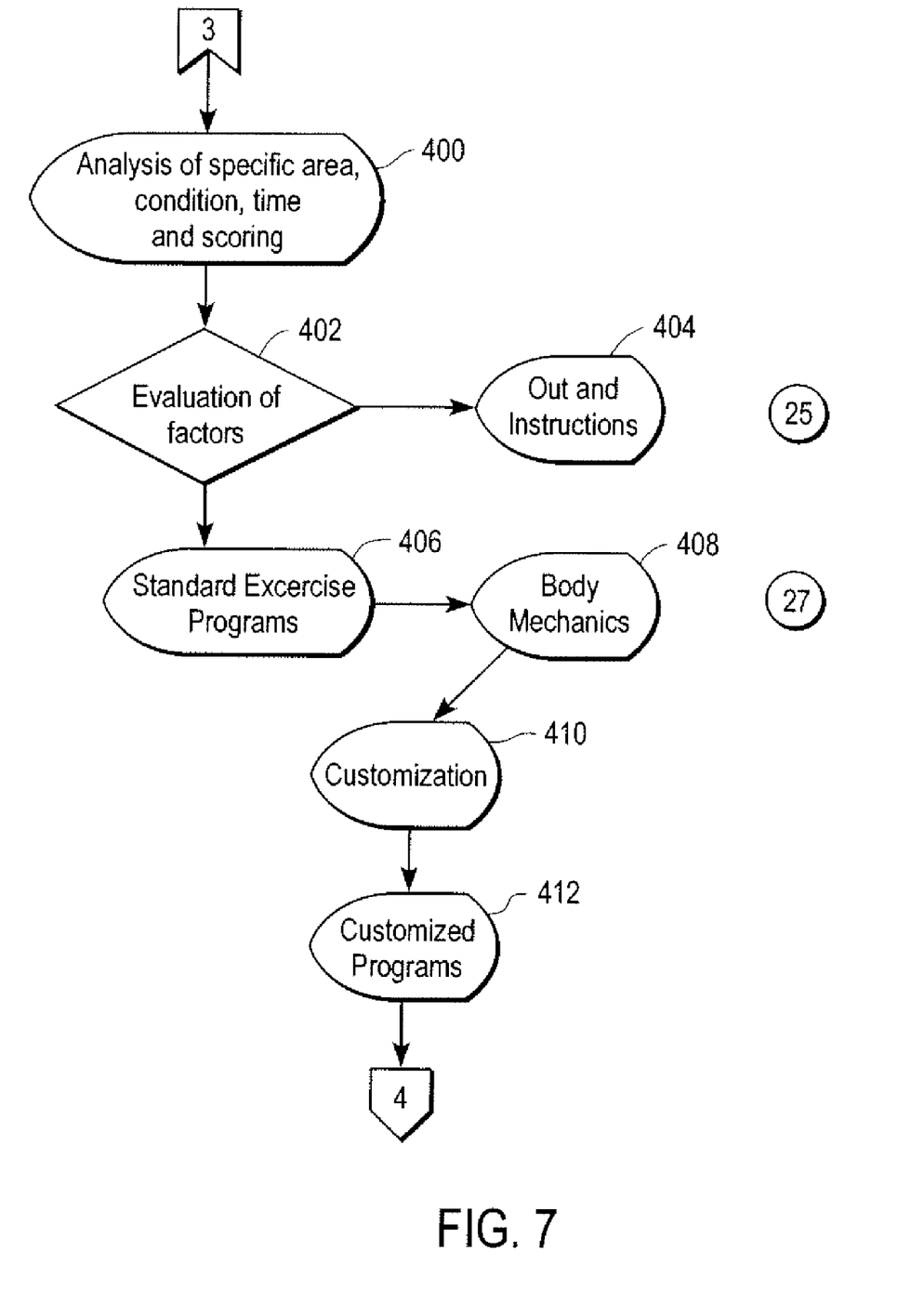
FIG. 7 is a flowchart showing the scoring of the assessment and determination and customization of exercise protocols in accordance with the teachings of the present invention.

The system will move the user to additional assessments to evaluate specific functional and physical capacities and capability related to a separate area of the program shown in FIG. 7. This same process from FIGS. 4 and 5 is used for initial and recurring assessments. The following is an example of the second assessment and the related individually weighted overall scoring.

Please answer the following questions regarding your ability to perform Activities of Daily Living (ADL).

Walking: Please walk using a normal foot & ankle motion and normal speed

50 - Unlimited on all surfaces
40 - Limited to 1 mile on incline and uneven surfaces
30 - Limited to 1 mile on flat, even surfaces
20 - Limited to less than ¼mile on flat surfaces
10 - Limited to less than 100 yards
 0 - Can't walk because of pain
Stairs: Please rate your ability to go up and down stairs 40 - Climbing up and down is normal with minimal pain
30 - Climbing up is normal, down is limited
20 - Climbing up and down is limited
10 - Need assistance to climb up/down stairs
 0 - Cannot climb stairs
Squatting: Squat down, you may allow your heels to rise off of the floor if necessary except on the 1$^{st}$ test 40 - Full squat with symmetrical weight bearing without assistance
30 - Full squat with compensation of weight bearing to non-painful side
20 - Full squat with assistance to stand up
10 - ½squat without compensation or assistance
 0 - Cannot squat
Balance: Do not use hand support, look straight ahead and stand only on the injured side. Use thick pillows for this test 40 - Can stand on 2 bed pillows for 1 minute, looking straight ahead
30 - Can stand on 1 pillow for 1 minute, looking straight ahead
20 - Can stand on the floor for 1 minute, looking straight ahead
10 - Can stand on the floor for 30-60 seconds while looking downward
 0 - Cannot stand on injured side for 30 seconds
Strength: Use light hand support for balance and standing on the injured foot, keep your knee straight throughout the test 40 - Perform 20–30 heel lifts, lifting all the way up onto the ball of your foot
30 - Perform 10–19 heel lifts
20 - Perform 5–9 heel lifts
10 - Perform 1–4 heel lifts
 0 - Cannot lift heel completely off of the ground
Strength: Standing, place your injured side heel on a 4-inch box about 10 inches in front of you 40 - Able to lift the front of your foot while keeping your heel down over 40 times
30 - Perform 30–39 times
20 - Perform 20–29 times
10 - Perform 10–19 times
 0 - Perform 0–9 times
Running: Please rate your ability to run using a normal foot action 40 - Can run, pivot and cut with mild discomfort
30 - Can run straight ahead only with mild discomfort
20 - Can run with a modified running pattern but painful
10 - Can hop on one foot but painful
 0 - Cannot run/hop because of pain and/or limited motion An example of Ankle Scoring is as follows:
0–30 = Phase 1
40–140 = Phase 2
150–280 = Phase 3
290–470 = Phase 4
Over 470 = Phase 5

At step 214, the system uses algorithms in order to evaluate assessment based on the specific area, condition, dates between assessments and other data. At step 216, the process of providing the user with a program continues based on the appropriate phase rating of care to be provided to the user, which is discussed in detail below with reference to FIG. 7. Thus, the system informs the user to seek advice from a healthcare provider in the event the analysis reveals that the user should be referred to the health care provider. Future assessment for a returning user or reassessment may result in a change of the protocol of care as appropriate. In some instances the user may have further injured the specific body area or may not have made sufficient progress to continue with the program. At the end of the reassessment, if the user's response to the questions reveals that the user is ready for the next phase, then the user is moved on to the appropriate phase or the next phase.

Referring now to FIG. 6, the process of providing care and or instructions to a user who has had surgery is shown. At step 300, the user enters the type and date of the surgery. The systems determines, based on the information provided by the user, if the surgery has occurred and if so how many days it has been since the surgery. At step 302, if the surgery has not occurred the user will be classified as pre-operative and the process moves to the assessment module of the program as shown in FIG. 5. At step 304, the system determines the Phase that the user will be at based on the number of days since the surgery. At step 306, the system will determine the appropriate goals to be achieved and determine the exercise and care plan based on the Phase allocated to the user and the process moves to the process as shown in FIG. 7.

FIG. 7 shows the process of beginning with instructions for the program of the standard phase of care based on the algorithms utilized in FIGS. 5 and 6. Based on the assessment or the type of surgery and days since surgery, the algorithms will determine a phase of care for the user. For example a standard care plan for ankle would include the following:
Introduction
Information for Area-Ankle
Maintain Balance/Strength/ROM range of motion
ICE as in cold how long and how many days
Information for Area—Foot
Protection
Exercise Referring now to FIG. 7, the process of scoring the assessment in order to customize the program for the user is based on the specific body area and phase of care for the user. At step 400, the system analyzes the specific area selected by the user, the condition of the area based on the phase allocation, and related time and scoring. At step 402, the system evaluates the factors, which can include medical history, demographics, and stage of maturity, relating to the user's condition and determines if the program needs to be adjusted or if the user should be instructed to stop the program or adjust the program. If so, then at step 404 the user is provided the necessary instructions and the process is routed to either instruct the user to stop the program or to reassess the condition of the user. If the user can continue and does not need to have the program readjusted, then at step 406 the user is provided a standard exercise program along with a care plan, at step 408, that will include instructions on activities of daily living, restrictions, exercise and typical healing process and times, programs are presented to the user. The user can accept this program as provided or at, step 410, customize the program based on specific exercises or customize regimes based on level of exercise, equipment available (bands, dumbbells, nothing, gym balls, etc.), goals (Range-Of-Motion or ROM, circulation, stabilization, agility, etc.), specific muscle, body area or type of movement (flexion, protraction, rotation) or any combination of the above. The customized programs can be saved for future utilization.

Figure 8:
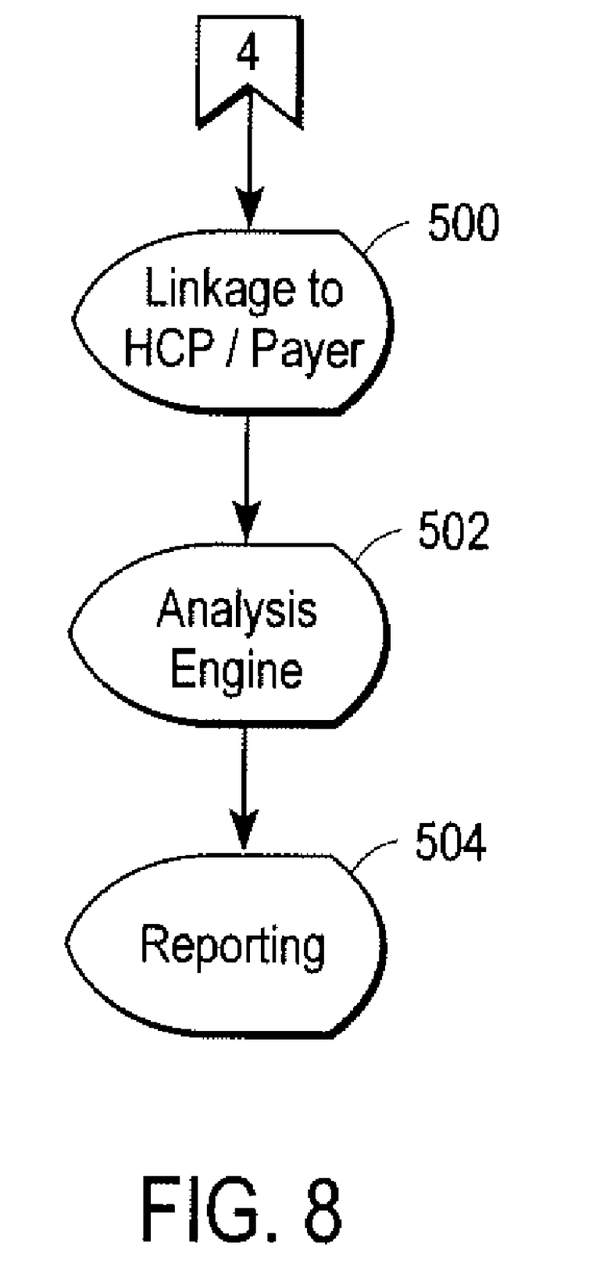
FIG. 8 is a flowchart showing the reporting and communication with the health care provider, payer and employer in accordance with the teachings of the present invention.

Referring now to FIG. 8, the process for the electronic communication between the system and health care providers (HCP), third party payers, employers and users begins at step 500. At step 500 a communication link is established between the health care provider and the system as well as third party payers as necessary. In one embodiment, the communication is automated and may be by Web, intranet, email, fax or phone or any other electronic communication. In an alternative embodiment, the users are prompted prior to establishing communication in order to determine if the communication link should be established. At step 502, the system uses the analysis database to analyze the medical and demographic information, as shown in FIG. 4, perform the assessments as shown in FIGS. 4 and 5, and surgery information provide during the process shown in FIG. 6. The analysis is utilized for various applications, such as outcome management for wellness, disease management, worker's compensation, reporting to healthcare providers, employers and third party payers. At step 504, the information and the analysis is reported to the appropriate party.

The foregoing detailed description of the invention has been presented for purposes of illustration and description. It is not intended to be exhaustive or to limit the invention to the precise form disclosed. Many modifications and variations are possible in light of the above teaching. The described embodiments were chosen in order to best explain the principles of the invention and its practical application to thereby enable others skilled in the art to best utilize the invention in various embodiments and with various modifications as are suited to the particular use contemplated.

What is claimed is:

1. A method for user centered self-assessment of a user, the method comprising the steps of:
    determining the user's targeted portion of the musculo-skeletal structure;
    electronically providing to the user at least one required physical action based on the targeted portion of the musculo-skeletal structure in order to determine the user's physical capability;
    evaluating the user's physical capacity based on a plurality of questions related to performance of the required physical action, wherein the responses to at least some of the questions have an assessment value;
    automatically analyzing the assessment values using an algorithm to determine a phase level for the user from a plurality of different phase levels associated with the user's targeted portion of the musculo-skeletal structure; and
    automatically determining at least one exercise protocol based on the phase level assigned to the user for improving the physical capacity.

2. The method of claim 1 further comprising:
    generating a post surgical exercise protocols using time based evaluations that occur post surgery.

3. The method according to claim 2 wherein the step of generating the post surgical exercise protocol includes the step of reevaluating the user's physical capacity by repeating at least one time the steps of evaluating, analyzing and determining in order to provide the user with an updated post surgical exercise protocol reflective of the user's improved physical capacity.

4. The method according to claim 2 further including the step of providing a care plan for the user to follow prior to surgical action.

5. The method according to claim 2 further including the step of providing a care plan for the user to follow after surgical action.

6. The method of claim 1 further comprising the step of gathering each response through a portable communication device.

7. The method of claim 1 further comprising the step of gathering each response using a remote connection to a central location, wherein the remote connection is through a virtual private network established over the Internet.

8. The method of claim 1 further comprising repeating at least one time the steps of determining, providing, evaluating, automatically analyzing and automatically determining, wherein the patient is provided with information sufficient to illustrate performance over time relative to previous results and to provide an updated protocol.

9. The method of claim 1 further including the step of storing the user's related demographical information, medical history, the assessment values and the phase level.

10. The method of claim 1, wherein each of the different phase levels has a different exercise protocol associated therewith.

11. The method according to claim 1 further including the step of reevaluating the user's physical capacity by repeating at least one time the steps of evaluating, analyzing and determining in order to provide the user with an updated exercise protocol.

12. The method according to claim 1 further including the step of providing a care plan for the user to follow.

13. A method of providing to a user a self-assessment for treatment of one of a plurality of physical conditions comprising the steps of:
   providing, at a central location, a list of medical and physical conditions and, for each physical condition an assessment that includes a plurality of questions, each question relating to an aspect of the physical condition, wherein:
      at least one of the questions requiring the person to perform a physical exercise and provide an answer relating to the results of the physical exercise, and
      at least other ones of the questions relate to general physical capabilities concerning the person's immediate past physical condition;
   forwarding, from a remote location chosen by the user that is different from the central location, an assessment request for the one physical condition;
   transmitting, from the central location to the remote location, the assessment for the one physical condition;
   recording, at the remote location, the answers to each of the plurality of questions for the one physical condition; and
   determining, based upon the answers and an algorithm that includes weights attributed to at least certain ones of the answers, a result of the assessment, wherein the result of the assessment includes a plurality of exercises directed toward improving the physical condition.

14. The method of claim 13 further comprising repeating a plurality of times the steps of providing, forwarding, transmitting, recording, and determining, wherein each time the step of providing occurs, presenting the user with information sufficient to illustrate performance over time that includes previous results.

15. The method according to claim 14, wherein the step of presenting modifies the presented menu each time based upon the results from the previous performance of the certain ones of the plurality of exercises, thereby ensuring that substantially different results will result in a different combination of exercises being presented.

16. The method according to claim 13, after the steps of providing, forwarding, transmitting, recording, and determining are repeated the plurality of times, further including the steps of:
   re-testing functional capability and physical capacity of the patient at the remote location, and wherein at least some of the results from the re-testing are electronically recorded and transmitted to the central location; and
   determining, at the central location, using at least the re-testing results and predetermined algorithms that relate test results to conditions, a revised assessment of the patient's condition.

17. The method according to claim 13 wherein the step of determining is performed in substantially real-time.

18. The method according to claim 13 further including the step of electronically communicating to the remote location the result of the assessment.

* * * * *